US00PP10207P

United States Patent [19]

Pieters

[11] Patent Number: Plant 10,207

[45] Date of Patent: Jan. 20, 1998

[54] CHRYSANTHEMUM PLANT NAMED 'TRIPOLI'

[76] Inventor: Dirk Pieters, Schierveldestraat 3A, Oosnieuwkerke, 8840 Staden, Belgium

[21] Appl. No.: 755,185

[22] Filed: Nov. 25, 1996

[51] Int. Cl.[6] ..... A01H 5/00

[52] U.S. Cl. ..... Plt./74.1

[58] Field of Search ..... Plt./74.1, 82.5, Plt./82.4

*Primary Examiner*—Howard J. Locker

*Attorney, Agent, or Firm*—C. A. Whealy

[57] ABSTRACT

A distinct cultivar of Chrysanthemum plant named 'Tripoli', characterized by its spherical and rounded plant habit; moderate growth rate and vigorous; multiple secondary laterals and numerous leaves; daisy-type inflorescences; purple ray florets with bright yellow disc florets; freely flowering; and good garden performance.

2 Drawing Sheets

The present invention relates to a new and distinct cultivar of garden Chrysanthemum plant, botanically known as *Dendranthema grandiflora* and referred to by the cultivar name 'Tripoli'.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor of the nonpatented cultivar 'Quick Marie' as the female, or seed, parent with the nonpatented cultivar 'Prisma' as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Tripoli'. These characteristics in combination distinguish 'Tripoli' as a new and distinct cultivar:

1. Spherical and rounded plant habit, moderate growth rate and vigorous.
2. Freely branching with secondary laterals and numerous leaves gives full, bushy appearance.
3. Daisy-type inflorescences.
4. Purple ray florets with bright yellow disc florets.
5. Freely flowering.
6. Good garden performance.

The cultivar 'Tripoli' has not been observed under all possible environmental conditions. The phenotype may vary somewhat with variations in environment such as temperature, daylength and light intensity, without, however, any variance in genotype.

In side-by-side comparisons in Staden, Belgium, under commercial practice, plants of the new Chrysanthemum differ from plants of the female parent, the cultivar 'Quick Marie', in plant size and inflorescence form and size. In the same comparisons, plants of the new Chrysanthemum differ from the male parent, the cultivar 'Prisma', in ray floret color, inflorescence form and plant size.

Plants of the new Chrysanthemum can be compared to the cultivar 'Stargazer' (U.S. Plant Pat. No. 5,695). However, in side-by-side comparisons conducted in Oxnard, Calif., under commercial practice, plants of the new Chrysanthemum differed from plants of the cultivar 'Stargazer' in the following characteristics:

1. Plants of the new Chrysanthemum are full, spherical and rounded whereas plants of the cultivar 'Stargazer' are upright.
2. Plants of the new Chrysanthemum are shorter than plants of the cultivar 'Stargazer'.
3. Plants of the new Chrysanthemum are more freely branching than plants of the cultivar 'Stargazer'. In addition, plants of the new Chrysanthemum have numerous secondary lateral branches.
4. Leaves of plants of the new Chrysanthemum are shorter but more numerous than leaves of plants of the cultivar 'Stargazer'.
5. Inflorescences of plants of the new Chrysanthemum are smaller, flatter and have fewer ray florets but are more numerous than inflorescences of plants of the cultivar 'Stargazer'.
6. Plants of the new Chrysanthemum have weaker and shorter peduncles than plants of the cultivar 'Stargazer'.

A detailed comparison of plants of the new Chrysanthemum and the cultivar 'Stargazer' appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Tripoli' with five cuttings in the container.

The second photograph comprises a close-up view of leaves at different stages of development and a fully opened inflorescence.

Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C., day temperatures ranging between 20 and 30C., and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar 'Tripoli'.

Commercial classification: Garden Chrysanthemum.

Parentage:

*Female, or seed, parent.*—*Dendranthema grandiflora* cultivar 'Quick Marie' (not patented).

*Male, or pollen, parent.*—*Dendranthema grandiflora* cultivar 'Prisma' (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Spherical and rounded growth habit. Moderate growth rate and vigorous. Freely branching with numerous secondary laterals.

*Plant height.*—About 17 cm.

*Lateral branch length.*—About 12 cm.

*Quantity of lateral branches after removal of apical meristem.*—About 5 with numerous secondary laterals.

*Stem color.*—147C.

*Foliage description.*—Number of leaves per plant: About 150. Number of leaves per lateral branch: Primary laterals: About 12. Secondary laterals: About 18. Leaf arrangement: Alternate. Leaf size, fully expanded: Length: About 4 cm. Width: About 3.8 cm. Leaf apex: Apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.3 cm. Color: Young foliage adaxial surface: 137A. Young foliage abaxial surface: 137C. Fully expanded foliage adaxial surface: 137A. Fully expanded foliage abaxial surface: 137C. Venation adaxial surface: 137A. Venation abaxial surface: 137C. Petiole: 137D.

Inflorescence description:

*Appearance.*—Daisy-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later. Inflorescences maintain good substance for three weeks under bright natural daylight.

*Quantity of inflorescences.*—About 7 to 10 inflorescences per flowering stem.

*Inflorescence size.*—Diameter: About 3.8 cm. Depth (height): About 7 mm. Diameter of disc: About 8 mm.

*Opening inflorescences.*—Bud shape: Spherical. Bud size: Length: About 6 mm. Width: About 6 mm. Bud color: 70A.

*Ray florets.*—Shape: Narrow, oblong. Size: Length: About 2.1 cm. Width: About 5 mm. Apex: Slightly tri-dentate. Base: Acute. Margin: Entire. Texture: Velvety, smooth and glabrous. Aspect: Oriented about 25° to the capitulum. Number of ray florets per inflorescence: About 26. Color: When opening, adaxial surface: 64B. When opening, abaxial surface: 70C. Mature, adaxial surface: 70A. Mature, abaxial surface: 70C. Fading to: 70C.

*Disc florets.*—Shape: Tubular. Size: Length: About 3 mm. Width: About 1 mm. Number of disc florets per inflorescence: About 76. Color: Immature: 154D. Mature: 154C.

*Peduncle.*—Aspect: Weak, wiry and angled about 20° to 25° to the stem. Length: First peduncle: About 2.5 cm. Fourth peduncle: About 4 cm. Texture: Pubescent. Color: 137C.

*Reproductive organs.*—Androecium: Present on disc florets only. Anther color: 5A. Pollen: Moderate, 5A in color. Gynoecium: Present on both ray and disc florets. Style color: 154C.

Disease resistance: No known Chysanthemum diseases observed to date on plants grown under commercial greenhouse conditions.

Seed production: Seed production has not been observed.

CHART A

| CHARACTERISTIC | 'TRIPOLI' | 'STARGAZER' |
|---|---|---|
| PLANT SHAPE | Spherical, rounded | Upright |
| GROWTH HABIT | Short | Medium |
| GROWTH RATE/VIGOR | Moderate/vigorous | Moderate/moderate |
| PLANT HEIGHT | About 17 cm | About 24 cm |
| LATERAL STEM LENGTH | About 12 cm | About 18 cm |
| QUANTITY OF LATERAL BRANCHES AFTER PINCHING | About 5 primary laterals and numerous secondary laterals | About 3 |
| STEM COLOR | 147C | 144A |
| LEAF LENGTH | About 4 cm | About 5 cm |
| LEAF WIDTH | About 3.8 cm | About 3.8 cm |
| PETIOLE LENGTH | About 2.3 cm | About 1.8 cm |
| QUANTITY OF LEAVES PER PLANT | About 150 | About 65 |
| YOUNG FOLIAGE COLOR, ADAXIAL SURFACE | 137A | 146A |
| YOUNG FOLIAGE COLOR, ABAXIAL SURFACE | 137C | 146B |
| MATURE FOLIAGE COLOR, ADAXIAL SURFACE | 137A | 147A |
| MATURE FOLIAGE COLOR, ABAXIAL SURFACE | 137C | 147B |
| QUANTITY OF INFLORESCENCES PER LATERAL STEM | About 7 to 10 | About 7 |
| INFLORESCENCE DIAMETER | About 3.8 cm | About 5 cm |
| INFLORESCENCE HEIGHT | About 7 mm | About 1.2 cm |
| BUD COLOR | 70A | 72A |
| RAY FLORET SHAPE | Narrow, oblong | Broad, obovate |
| RAY FLORET LENGTH | About 2.1 cm | About 2.2 cm |
| RAY FLORET WIDTH | About 5 mm | About 7 mm |
| RAY FLORET ORIENTATION | Slightly upright | Horizontal |
| RAY FLORET COLOR, WHEN OPENING, ADAXIAL | 64B | 64A |
| RAY FLORET COLOR, WHEN OPENING, ABAXIAL | 70C | 64B |
| RAY FLORET COLOR, MATURE, ADAXIAL | 70A | 70B |
| RAY FLORET COLOR, MATURE, ABAXIAL | 70C | 75C |
| RAY FLORET COLOR FADING TO | 70C | 70C |
| NUMBER OF RAY FLORETS PER INFLORESCENCE | About 26 | About 60 |
| DISC FLORET COLOR, | 154D | 2C |

-continued

CHART A

| CHARACTERISTIC | 'TRIPOLI' | 'STARGAZER' |
|---|---|---|
| IMMATURE DISC FLORET COLOR, MATURE | 154C | 2C |
| DIAMETER OF DISC | About 8 mm | About 1 cm |
| NUMBER OF DISC FLORETS PER INFLORESCENCE | About 76 | About 114 |
| PEDUNCLE STRENGTH | Weak, wiry | Strong |
| PEDUNCLE LENGTH, FIRST | About 2.5 cm | About 6.2 cm |

-continued

CHART A

| CHARACTERISTIC | 'TRIPOLI' | 'STARGAZER' |
|---|---|---|
| PEDUNCLE LENGTH, FOURTH | About 4 cm | About 8.5 cm |
| PEDUNCLE COLOR | 137C | 146C |
| ANTHER COLOR | 5A | 12A |
| POLLEN COLOR | 5A | 12A |

It is claimed:

1. A new and distinct cultivar of Chrysanthemum plant named 'Tripoli', as illustrated and described.

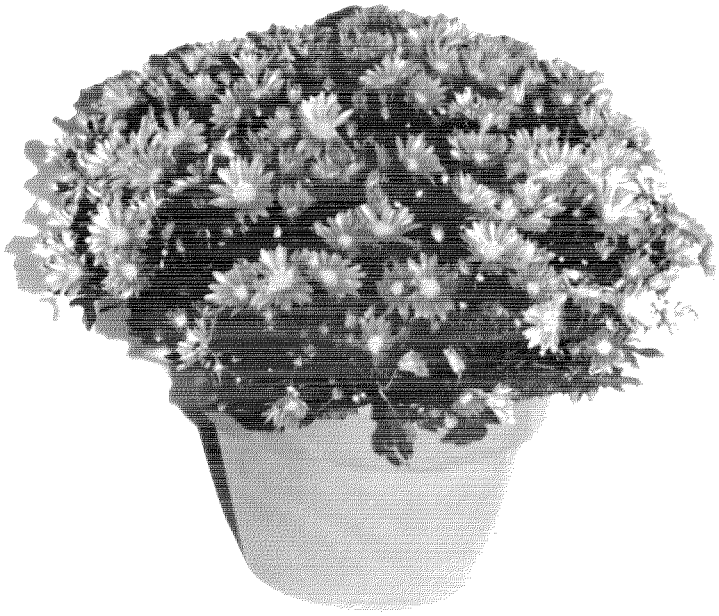

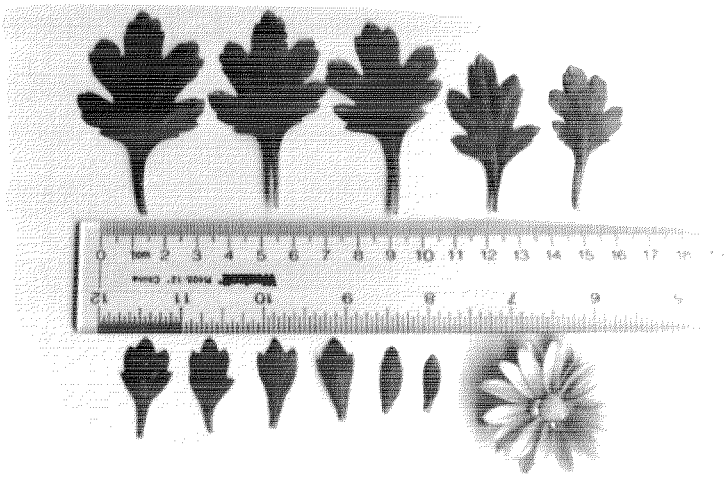

* * * * *